(12) United States Patent
Cresina

(10) Patent No.: US 8,096,998 B2
(45) Date of Patent: Jan. 17, 2012

(54) EXTERNAL FIXATION TENSIONER

(75) Inventor: Jeffery Cresina, Middlesex, NJ (US)

(73) Assignee: EBI, LLC, Parsippany, NJ (US)

( * ) Notice: Subject to any disclaimer, the term of this patent is extended or adjusted under 35 U.S.C. 154(b) by 1065 days.

(21) Appl. No.: 11/861,446

(22) Filed: Sep. 26, 2007

(65) Prior Publication Data

US 2009/0082776 A1  Mar. 26, 2009

(51) Int. Cl.
*A61B 17/70* (2006.01)

(52) U.S. Cl. ..................... 606/103; 606/86 A

(58) Field of Classification Search ............ 606/74, 606/86 R, 86 A, 103, 246–279; 254/245–247
See application file for complete search history.

(56) References Cited

U.S. PATENT DOCUMENTS

| | | |
|---|---|---|
| 2,889,085 A | 6/1959 | Collins |
| 3,975,032 A | 8/1976 | Bent et al. |
| 4,091,880 A | 5/1978 | Troutner et al. |
| 4,140,111 A | 2/1979 | Morrill |
| 4,441,563 A | 4/1984 | Walton, II |
| 5,248,068 A | 9/1993 | Goergen et al. |
| 5,312,410 A * | 5/1994 | Miller et al. ............. 606/86 R |
| 5,483,952 A | 1/1996 | Aranyi |
| 5,496,327 A | 3/1996 | Den Ouden et al. |
| 5,507,727 A | 4/1996 | Crainich |
| 5,609,596 A | 3/1997 | Pepper |
| 5,643,319 A | 7/1997 | Green et al. |
| 5,902,306 A | 5/1999 | Norman |
| 6,042,585 A | 3/2000 | Norman |
| 6,689,140 B2 | 2/2004 | Cohen |
| 7,094,240 B2 | 8/2006 | Molz, IV et al. |
| 2002/0072753 A1 * | 6/2002 | Cohen .................. 606/103 |
| 2005/0149086 A1 * | 7/2005 | Huxel et al. ............. 606/167 |

FOREIGN PATENT DOCUMENTS

WO   WO-9009150   8/1990

\* cited by examiner

*Primary Examiner* — Eduardo C Robert
*Assistant Examiner* — Summer Kostelnik
(74) *Attorney, Agent, or Firm* — Harness, Dickey

(57) ABSTRACT

A tensioner for tensioning a wire/cable coupled to an external orthopedic device. The tensioner can include a housing, an outer sleeve movable relative to the housing, a movable tension actuator handle operable to move the outer sleeve relative to the housing, and a plurality of movable jaws supported in the outer sleeve. The jaws can move between an open position for receiving the wire/cable and a closed position for gripping the wire/cable when the tension actuator handle is operated.

16 Claims, 6 Drawing Sheets

EXTERNAL FIXATION TENSIONER

Various external fixation devices are known for positioning bone portions relative to one another or tensioning bone for promoting bone growth in trauma. The external fixation device can include ring portions around the affected body portion, and wires or cables connected to the ring portions with clamps for exerting forces on the bone portions. The wires or cables can be tensioned using known tensioners.

The present teachings provide an ergonomic tensioner that can be used with wires and/or cables of different sizes. The tensioner provides automatic locking and can be easily calibrated.

SUMMARY

The present teachings provide a tensioner for tensioning a wire/cable coupled to an external orthopedic device.

In one aspect, the tensioner can include a housing, an outer sleeve coupled to and movable relative to the housing, and a plurality of movable jaws received in the internal bore and engageable with the wire/cable. The outer sleeve can have an internal bore and an outer surface with a ratcheted portion. The tensioner can further include a pawl engageable with the ratcheted portion of the outer sleeve, and a tension actuator handle coupled to the pawl. The tension actuator handle can rotate relative to the housing for moving the outer sleeve relative to the housing and tensioning the wire/cable.

In another aspect, the tensioner can include a housing, an outer sleeve movable relative to the housing, a movable tension actuator handle operable to move the outer sleeve relative to the housing, and a plurality of movable jaws supported in the outer sleeve. The jaws can move between an open position for receiving the wire/cable and a closed position for gripping the wire/cable when the tension actuator handle is operated.

In another aspect, the tensioner can include a handle body including a pistol grip handle and an upper cylindrical housing defining a longitudinal slot, a tension actuator handle pivotably coupled to the handle body, a handle spring coupled to the handle body and biasing the tension actuator handle away from the pistol grip handle, and a pawl pivotably coupled to the tension actuator handle. The tensioner can further include a containment sleeve received in the cylindrical housing, a plurality of spring washers received in the containment sleeve, a gauge collar connected to a proximal end of the containment sleeve, and an outer sleeve coupled to and movable relative to the housing, the outer sleeve having a proximal ratcheted surface. The tensioner can also include a movable jaw-retaining tubular shaft received in a distal portion of the outer sleeve, a plurality of movable jaws supported in a tapered portion of the jaw-retaining shaft, a movable tubular post passing through the gauge collar, the spring washers and the jaw-retaining shaft, and a jaw spring biasing the jaws in a closed position.

Further areas of applicability of the present teachings will become apparent from the description provided hereinafter. It should be understood that the description and specific examples are intended for purposes of illustration only and are not intended to limit the scope of the present teachings.

BRIEF DESCRIPTION OF THE DRAWINGS

The present teachings will become more fully understood from the detailed description and the accompanying drawings, wherein.

DESCRIPTION OF VARIOUS ASPECTS

Figure 1:
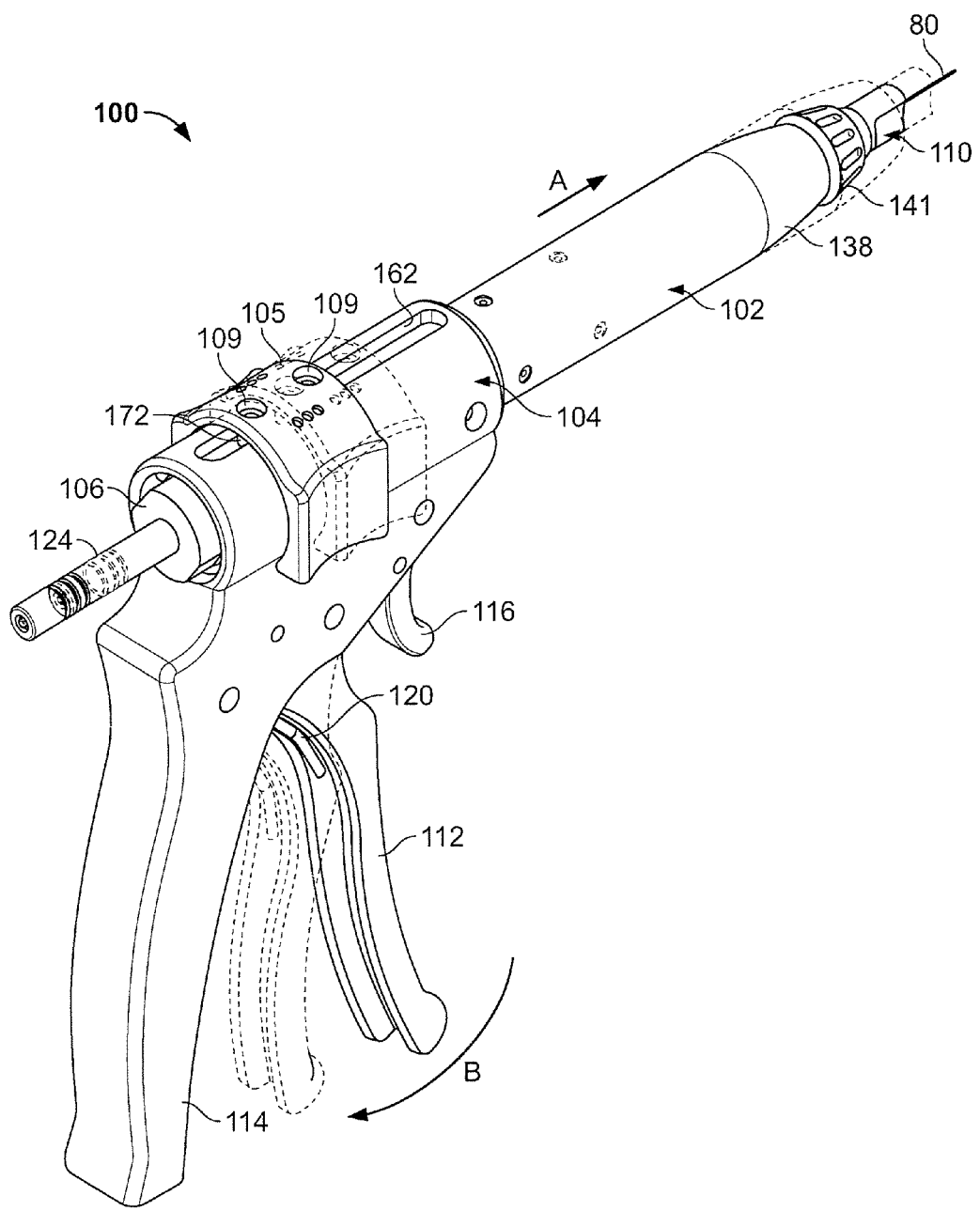
FIG. 1 is a perspective view of an external fixation tensioner according to the present teachings.
Figure 2:
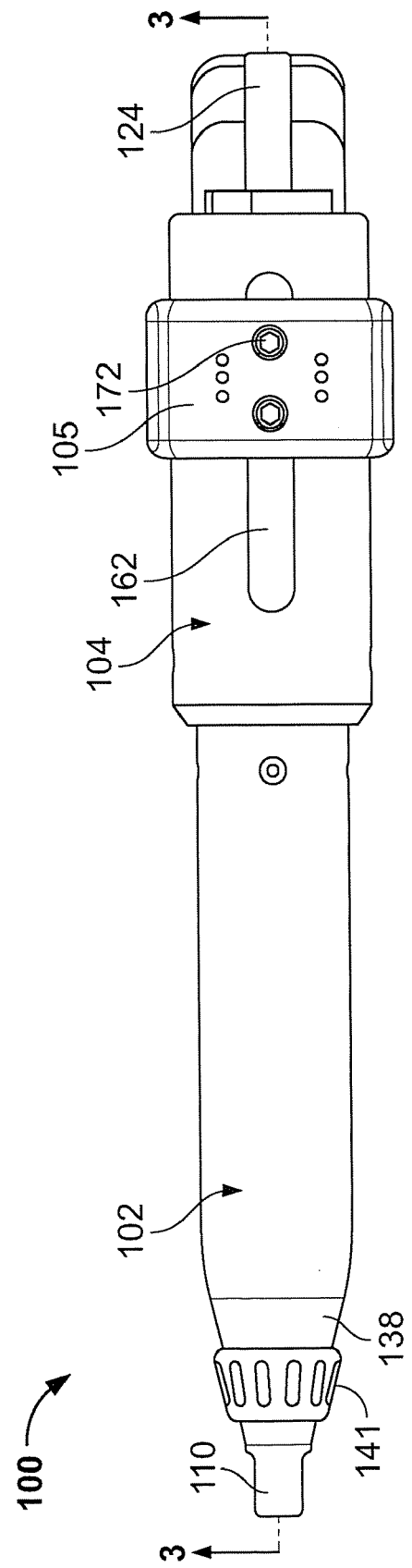
FIG. 2 is a top view of the external fixation tensioner of FIG. 1.

The following description is merely exemplary in nature and is in no way intended to limit the present teachings, applications, or uses. For example, the present teachings can be used for tensioning any wires and cables used in connection with orthopedic surgery, including tensioning wire and cable systems associated with the external fixation devices.

Referring to FIGS. 1-6, an exemplary external fixation tensioner 100 according to the present teachings can include an outer sleeve 102, and a handle body 104 with first and second ergonomic handles 112, 114 biased in an a spaced-apart position by a handle spring 120. The tensioner 100 can also include a release trigger 116, a gauge collar 106, a slide stop 105, and an elongated tubular spring post 124. The first and second handles can be ergonomically shaped. As illustrated, the first handle 112 can operate as a movable or tension actuator handle 112 for tensioning a wire/cable 80, and the second handle 114 can operate as a fixed or pistol grip handle 114. In combination, the tension actuator handle 112 and the pistol grip handle allow the user to hold and operate the tensioner 100 with one hand only, as discussed below.

Figure 4:
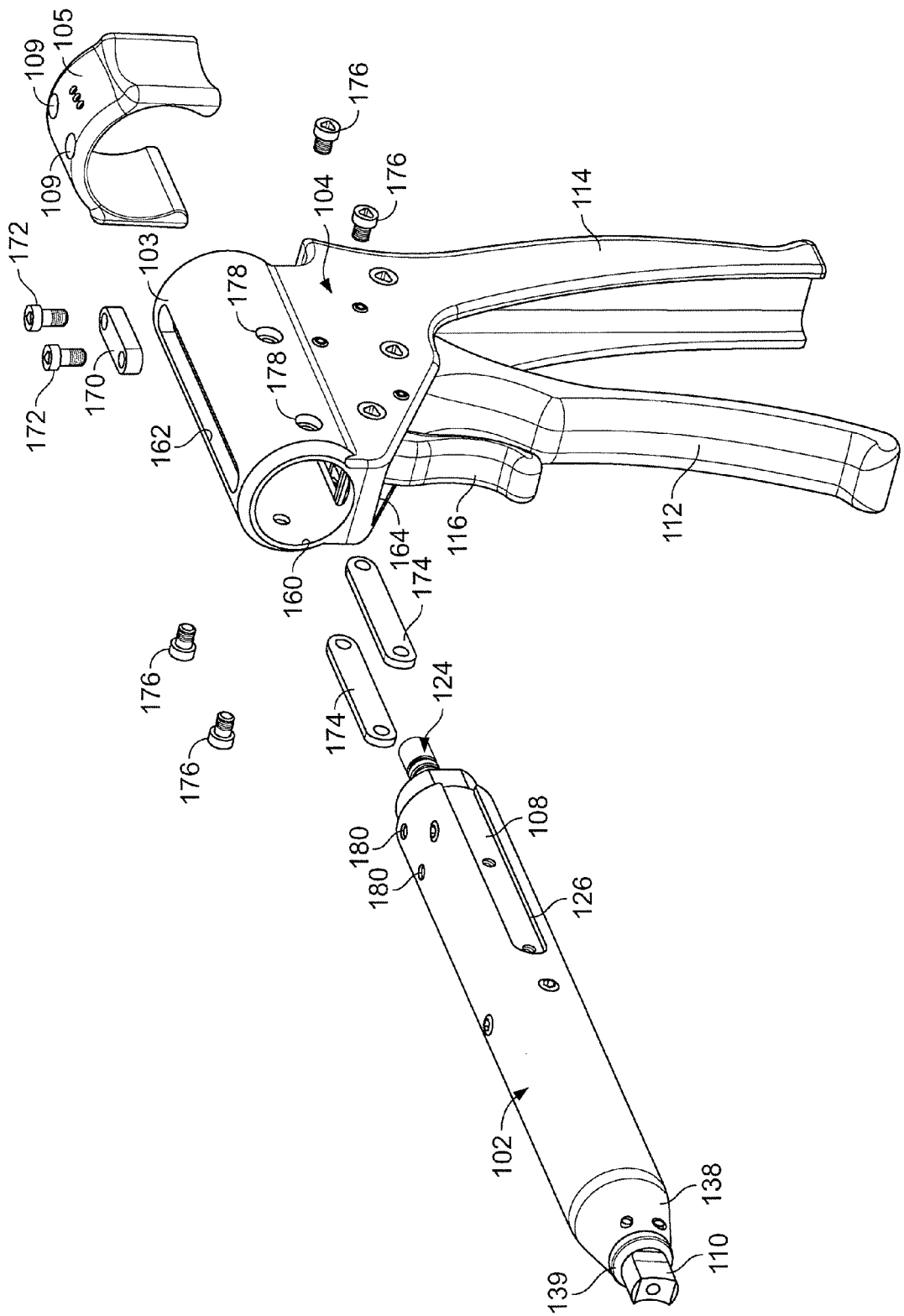
FIG. 4 is a partially exploded view of an external fixation tensioner according to the present teachings.
Figure 5:
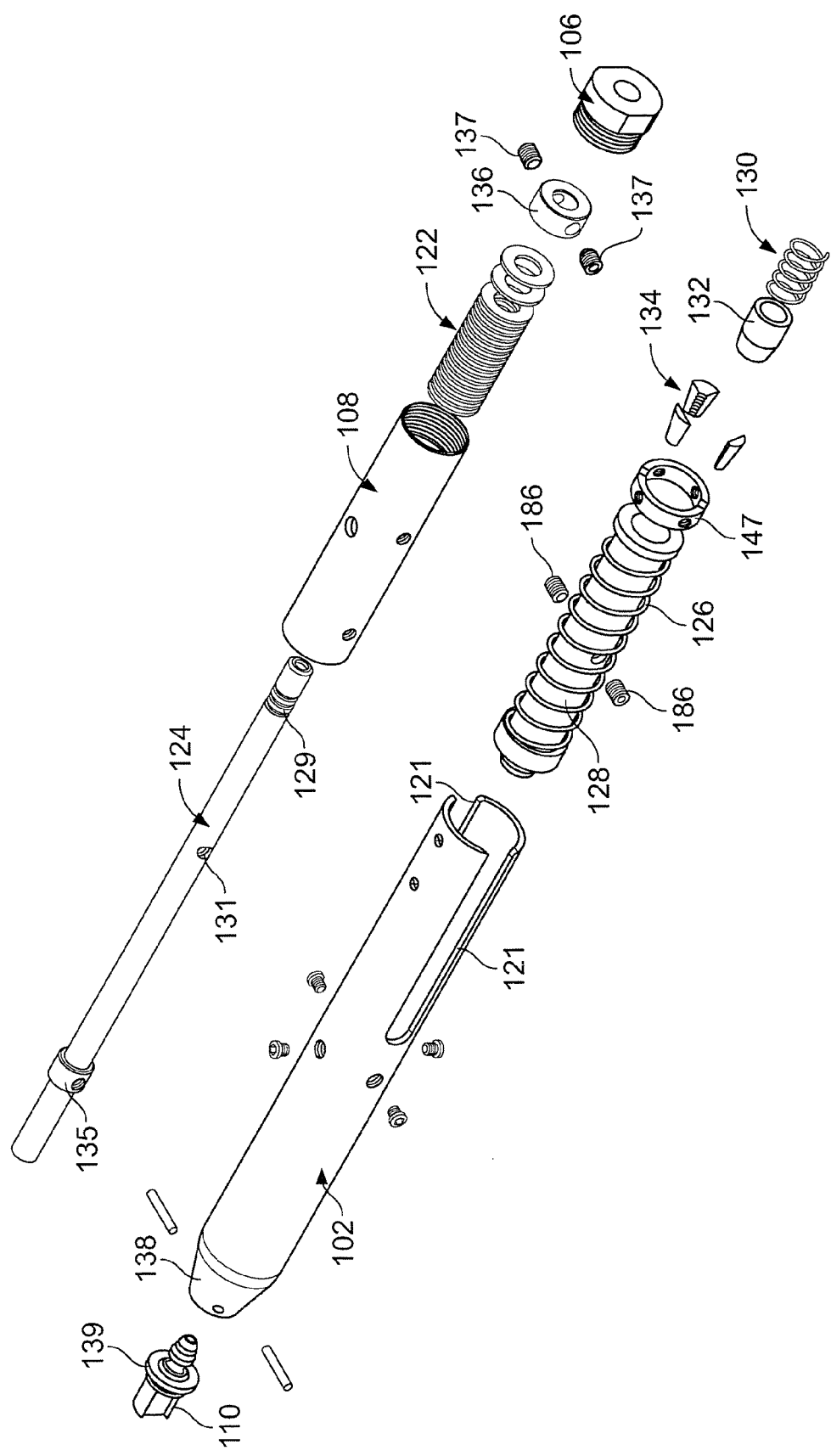
FIG. 5 is an exploded view of a first portion of the external fixation tensioner of FIG. 4.
Figure 6:
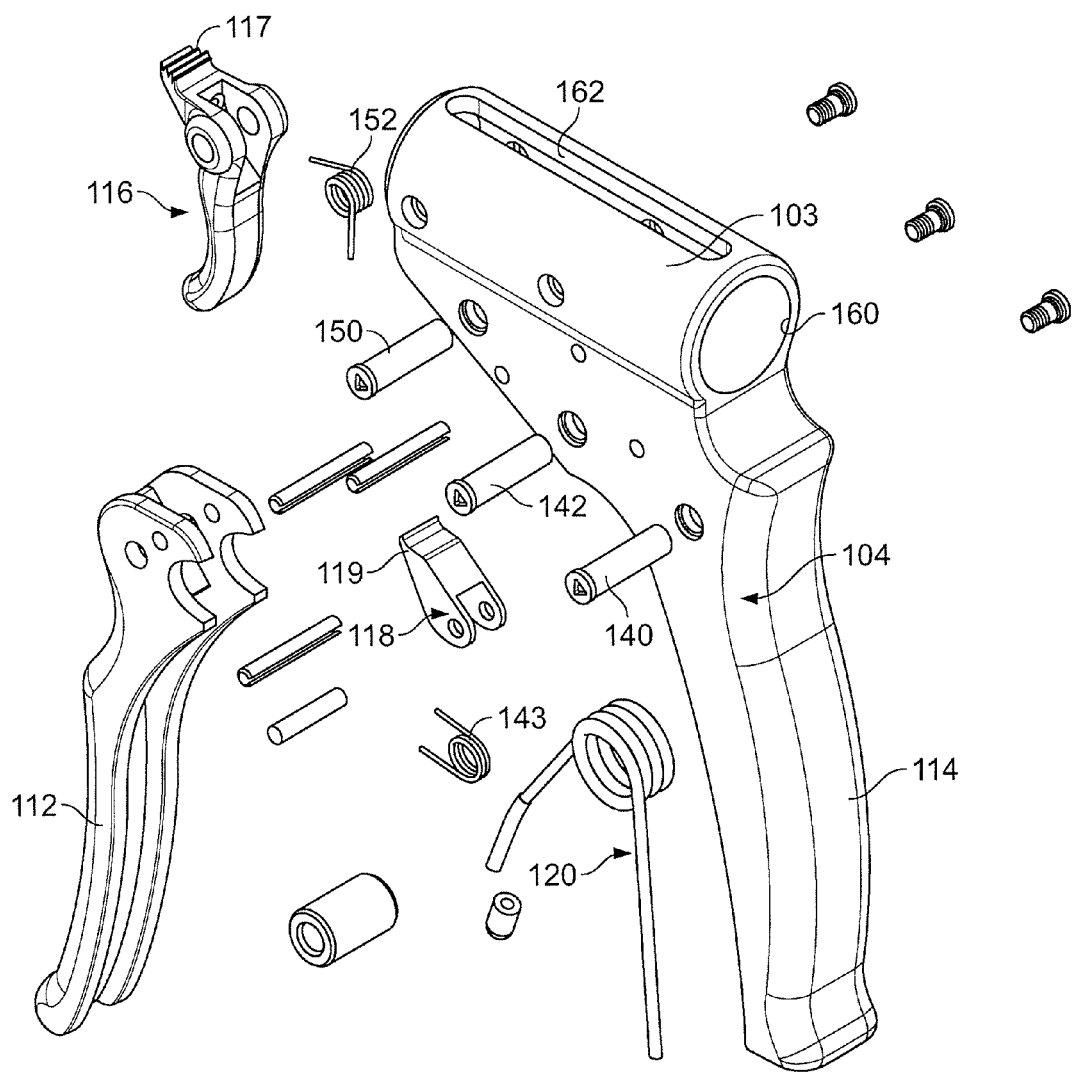
FIG. 6 is an exploded view of a second portion of the external fixation tensioner of FIG. 4.

Referring particularly to FIGS. 4-6, the outer sleeve 102 can be structurally configured in shape and size for receiving various components, as shown in the exploded view of FIG. 5. Similarly, the handle body 104 can be structurally shaped and sized to receive or support various components, as shown in the exploded view of FIG. 6. The outer sleeve 102 and the handle body 104 can be connected as shown in FIG. 4 and discussed below.

Figure 3:
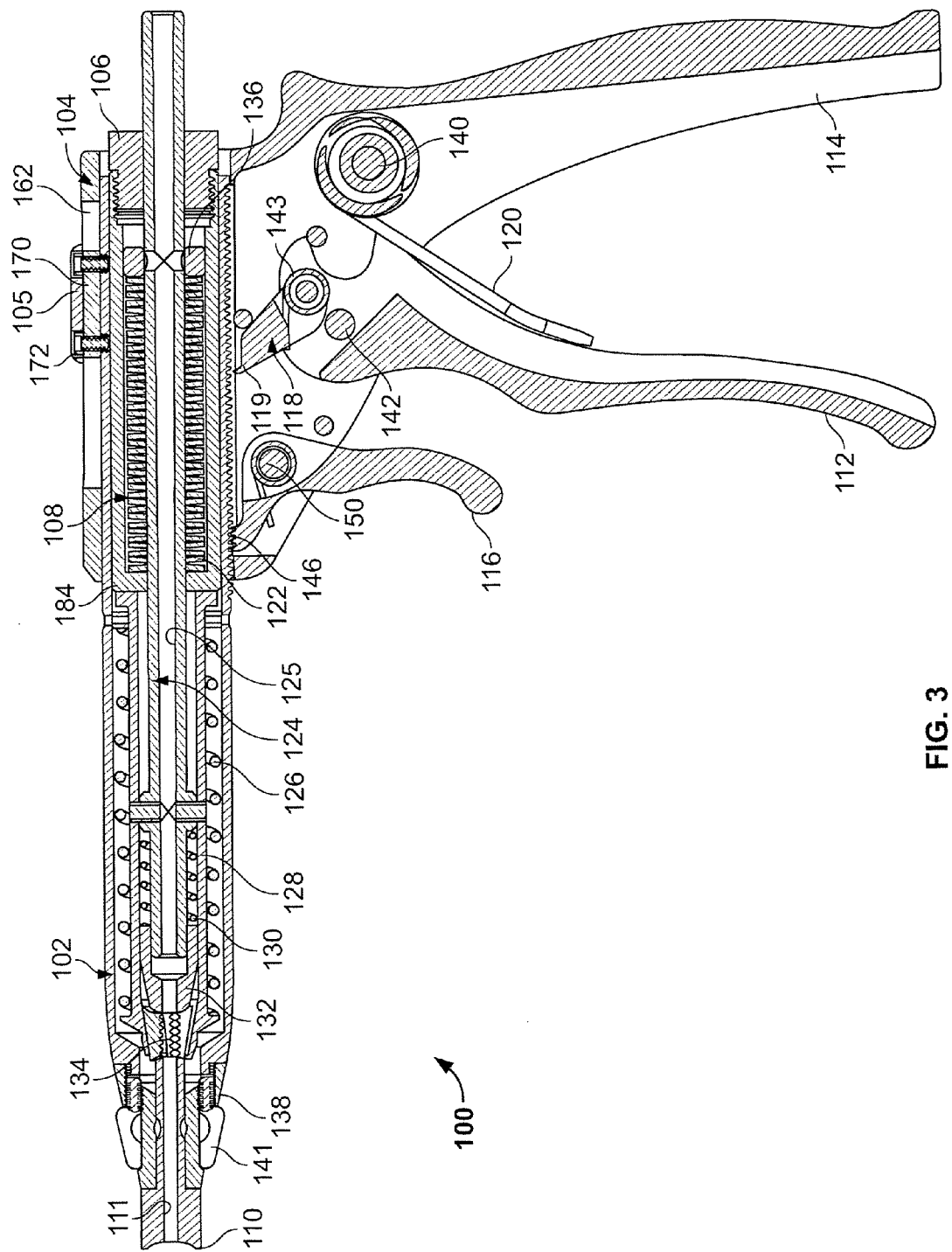
FIG. 3 is a sectional view of the external fixation tensioner of FIG. 2 taken along the line 3-3.

More specifically, and referring to FIGS. 3 and 5, the outer sleeve 102 can include a tapered conical portion 138 and a wire- or cable-receiving tensioning nose or tip 110. The tensioning nose 110 can have an inner longitudinal bore 111, and can be connected to the outer sleeve 102 with a coupler 139, such as a ring and pins, and/or a chuck 141, for example. The outer sleeve 102 can have a ratcheted surface or rack 146 machined on a portion of its proximal outer surface, which is positioned adjacent to the handle body 104, as discussed below. The outer sleeve 102 can receive a tubular jaw-retaining shaft 128 having an outer sleeve spring 126 around its outer surface, and a containment sleeve 108 that houses a plurality of Belleville or other annular spring washers 122. The spring washers 122 can operate as springs that convey wire tension information by converting distance increment information to corresponding load increment information. Using the spring washers 122, the tensioner 100 can be calibrated for tensions of 70 kg (686.5 N), 100 kg (980.7 N), and 130 kg (1284.9 N), for example.

A gauge collar 106 can be threadably connected to a proximal end of the containment sleeve 108 to provide a reference datum for tension markings 129 on the proximal end of the spring post 124 to convey the amount of tension on the wire/cable using the Belleville washer conversion information as the spring post 124 moves relative to the handle body 104. It will be appreciated that the spring washers 122 can be replaced with other springs or biasing members that are similarly operable.

The spring post 124 can be tubular with an inner longitudinal bore 125 and can extend through the gauge collar 106, the spring washers 122 in the containment sleeve 108, and the jaw-retaining shaft 128. A set of spaced-apart wire/cable gripping jaws 134 can be captured in a tapered distal portion of the jaw-retaining shaft 128. A jaw spring 130 can surrounds a distal portion of the spring post 124 and be captured between a tubular tapered connector 132 connected to the spring post 124 and a tubular spring stop 135 around the spring post 124. The jaws 134 can have serrated gripping surfaces and can be biased in an open or non-gripping position by the tensioning nose 110 and the tapered connector 132, thereby compressing the jaw spring 130. Although three spaced-apart jaws 134 are shown in FIG. 5, fewer or more than three jaws 134 can also be used. A tubular ring 136 adjacent the most proximal of the spring washers 122 can be connected to the spring post 124 through fasteners 137 at openings 131 to provide a washer stop, such that forward movement of the spring post 124 can compress the spring washers 122 against a distal end abutment 184 of the containment sleeve 108. Similarly, fasteners 186 can couple the jaw-retaining shaft 128 to the spring stop 135 of the spring post 124.

Referring to FIGS. 3 and 6, the handle body 104 can be a hollow member including a cylindrical or other tubular housing 103 having a bore 160 adapted to receive the containment sleeve 108 and a portion of the outer sleeve 102 surrounding the containment sleeve 108. The housing 103 can include an elongate through-slot 162 defined on an upper portion of the surface of the cylindrical housing. The handle body 104 can be integrally coupled to the pistol grip handle 114. The tension actuator handle 112 can be movably connected to the handle body 104 with a pin or other pivot element 142 and can be biased away from the pistol grip handle 114 by the handle spring 120. The handle spring 120 can be connected to the pistol grip handle 114 with a pin or other pivot element 140. The tension actuator handle 112 can function as a tension actuator for the wire or cable 80, which can be received through the bore 111 of the tensioning nose 110 and gripped by the jaws 134, as discussed below. The tension actuator handle 112 can support a pawl 118 having an engagement extension 119, which can engage the rack 146 of the outer sleeve 102 through a lower opening 164 of the handle body 104. The pawl 118 can be rotatably coupled to the tension actuator handle 112 and biased with pawl spring 143.

Referring to FIGS. 3, 4 and 6, the handle body 104 can rotatably support a release trigger 116 rotatably biased with a trigger spring 152 coupled to a pin or other pivot element 150. The release trigger 116 can include teeth or other engagement projections 117 for engaging the rack 146 of the outer sleeve 146. The release trigger 116 can engage the rack 146 through the lower opening 164 of the handle body 104. The slide stop 105 can be slidably coupled on the outer surface of the housing 103 and connected to the containment sleeve 108 with fasteners 172 passing through openings 109 of the slide stop 105, through a slider plate 170 received in the slot 162, and through corresponding opening 180 of the outer sleeve 102. The slide stop 105 can travel with the slider plate 170 in the slot 162 and limit the extent of travel of the outer sleeve 102 to the length of the slot 162.

The outer sleeve 102 can include a pair elongated side slots 121 defined in a proximal portion of the outer sleeve 102. Two elongated plates 174 can be received through the slots 121 to attach the containment sleeve 108 to the housing 103 with fasteners 176 passing through openings 178 of the housing 103, as shown in FIG. 4.

In operation, and referring to FIGS. 1 and 3, a wire/cable 80 that is secured on an external fixation device (not shown) can be inserted into the bore 111 of the tensioning nose 110. The tensioner 100 can be held by the user at the pistol grip handle 114, and the tension actuator handle 112 can be pulled back toward the pistol grip handle 114 against the bias of the handle spring 120 in the direction of curved arrow B, as shown in FIG. 1. Pulling back the tension actuator handle 112 engages the pawl 118 to the rack 146 of the outer sleeve 102, and forces the outer sleeve 102 forward in the direction of arrow A, increasing the overall length of the tensioner 100, as shown in phantom in FIG. 1, thereby pulling on the wire/cable 80, and creating tension. Repeated pulling of the tension actuator handle 112 can incrementally achieve a desired tension on the wire/cable 80.

When the outer sleeve 102 moves forward, the containment sleeve 108 can remain fixed within the housing 103, while the jaw-retaining shaft 128 and the spring post 124 can move forward with the outer sleeve 102. In particular, when the outer sleeve 102 is pushed away from the housing 103 by the action of the pawl 118, the outer sleeve spring 126 is compressed, and the jaws 134 are pushed forward by the action of the jaw spring 130, which is released from its compressed state by the increase in length between the tensioning nose 110 and the tapered connector 132. The jaws 134 can be forced to close around and grip the wire/cable 80 by the jaw spring 130. Repeated action forces the jaws 134 forward onto the wire/cable 80, increasing the tension of the wire/cable 80. The spring-biased jaws 134 can accommodate different diameters of wires and or cables automatically as the jaws 134 close around and grip the wire/cable 80 when the tension actuator handle 112 is squeezed. For certain applications, the tensioner can automatically adjust and lock on wires/cables from about 1.6 mm to about 2.5 mm in diameter.

The spring post 124 and the ring 136 can move relative to the gauge collar 124 as the tension actuator handle 112 is squeezed. The forward movement of the spring post 124 can compress the spring washers 122 in the containment sleeve 108 between the ring 136 and the abutment 184. The distance of the tension markings 129 of the spring post 124 from the gauge collar 106 can provide an indication of the magnitude of the tension applied to the wire/cable 80. The slide stop 105 moves with the outer sleeve 102, and the slider plate 170 travels along the slot 162, such that the total travel of the outer sleeve 102 is constrained by the extent of the slot 162.

After the wire/cable 80 has been tensioned to the desired load level, the wire/cable can be secured to the external fixation device to prevent loss of tension, and disconnect the tensioner 100. The tension actuator handle 112 can be slightly squeezed to allow the release trigger 116 to be easily pulled. Pulling the release trigger 116 can quickly release the tension and free the secured wire/cable 80 from the tensioner 100. Accordingly, the outer sleeve spring 126 can pull the outer sleeve 102 back to its initial position returning the tensioner 100 to its original non-extended position and shorter length. The jaw-retaining shaft 128, the jaws 134, the spring post 124 and the tensioning nose 110 can also move back to their initial positions, and the jaws 134 can be forced open by the tensioning nose 110, thereby compressing the jaw spring 130. In this position, the jaws 134 are ready to receive a wire/cable 80 and tensioner 100 is ready to be used again to tension a wire/cable 80.

It will be appreciated that tensioner 100 can advantageously be held and operated using a single hand only. The wire/cable 80 can be gripped and tensioned in a single caulk-gun type familiar action, and the tension can be simultaneously read at the proximal end of the tensioner 100. Additionally, the tensioner 100 can automatically adjust to gripping and tensioning wires or cables of different diameters by a single gripping action of the jaws 124. Accordingly, the tensioner 100 can be used in different applications in a time-saving, ergonomic and an efficient manner.

The foregoing discussion discloses and describes merely exemplary arrangements of the present teachings. One skilled in the art will readily recognize from such discussion, and from the accompanying drawings and claims, that various changes, modifications and variations can be made therein without departing from the spirit and scope of the present teachings as defined in the following claims.

What is claimed is:

1. A tensioner for tensioning a wire/cable coupled to an external orthopedic device, the tensioner comprising:
   a housing;
   an outer sleeve coupled to and movable relative to the housing, the outer sleeve having an internal bore and an outer surface with a ratcheted portion;
   a plurality of movable jaws received in the internal bore and engageable with the wire/cable;
   a pawl engageable with the ratcheted portion of the outer sleeve;
   a tension actuator handle coupled to the pawl, the tension actuator handle rotatable relative to the housing for moving the outer sleeve relative to the housing and tensioning the wire/cable; and
   a slide stop limiting movement of the outer sleeve, the slide stop being slidably coupled to the housing.

2. The tensioner of claim 1, wherein the plurality of jaws is movable from an open position to a closed gripping position by rotation of the tension actuator handle.

3. The tensioner of claim 1, further comprising:
   a jaw spring; and
   a tubular post supporting the jaw spring and coupled to the jaws, the post received in the internal bore of the outer sleeve and the post movable relative to the housing.

4. The tensioner of claim 3, wherein the plurality of jaws includes three spaced-apart jaws.

5. The tensioner of claim 4, wherein the housing movably receives a proximal portion of the outer sleeve.

6. The tensioner of claim 1, further comprising a release trigger engageable with the ratcheted surface of the outer sleeve.

7. The tensioner of claim 1, further comprising a slider plate coupled to the slide stop and the outer sleeve, the slider plate movable in a through slot of the housing.

8. The tensioner of claim 1, further comprising:
   a pistol grip handle connected to the housing; and
   a handle spring biasing the tension actuator handle away from the pistol grip handle.

9. The tensioner of claim 1, wherein the jaws are biased in an open position.

10. The tensioner of claim 1, further comprising:
    a jaw-retaining shaft having a longitudinal bore with a tapered distal end, the jaw-retaining shaft supporting the plurality of jaws and received in the outer sleeve; and
    an outer sleeve spring coupled to the jaw-retaining shaft.

11. A tensioner for tensioning a wire/cable coupled to an external orthopedic device, the tensioner comprising:
    a housing;
    an outer sleeve coupled to and movable relative to the housing, the outer sleeve having an internal bore and an outer surface with a ratcheted portion;
    a plurality of movable jaws received in the internal bore and engageable with the wire/cable;
    a pawl engageable with the ratcheted portion of the outer sleeve;
    a tension actuator handle coupled to the pawl, the tension actuator handle rotatable relative to the housing for moving the outer sleeve relative to the housing and tensioning the wire/cable;
    a gauge collar coupled to the housing; and
    a plurality of annular spring washers received in the housing.

12. A tensioner for tensioning a wire/cable coupled to an external orthopedic device, the tensioner comprising:
    a housing;
    an outer sleeve movable relative to the housing;
    a movable tension actuator handle operable to move the outer sleeve relative to the housing;
    a plurality of movable jaws supported in the outer sleeve, the jaws movable between an open position for receiving the wire/cable and a closed position for gripping the wire/cable when the tension actuator handle is operated; and
    a travel delimiter including:
       a slide stop coupled to the housing; and
       a slider plate received in a longitudinal slot of the housing and coupled to the slider stop and the outer sleeve.

13. The tensioner of claim 12, further comprising a pawl coupled to the tension actuator handle and engageable with a ratcheted surface of the outer sleeve.

14. The tensioner of claim 12, further comprising:
    a tubular post coupled to the jaws and movable relative to the housing; and
    a jaw spring biasing the jaws in the closed position.

15. A tensioner for tensioning a wire/cable coupled to an external orthopedic device, the tensioner comprising:
    a housing;
    an outer sleeve movable relative to the housing;
    a movable tension actuator handle operable to move the outer sleeve relative to the housing;
    a plurality of movable jaws supported in the outer sleeve, the jaws movable between an open position for receiving the wire/cable and a closed position for gripping the wire/cable when the tension actuator handle is operated; and
    a tension measuring device including:
       a gauge collar;
       a plurality of spring washers; and
       tension markings on a proximal end of the post.

16. A tensioner for tensioning a wire/cable coupled to an external orthopedic device, the tensioner comprising:
    a handle body including an upper cylindrical housing and a pistol grip handle, the cylindrical housing defining a longitudinal slot;
    a tension actuator handle pivotably coupled to the handle body;
    a handle spring coupled to the handle body and biasing the tension actuator handle away from the pistol grip handle;
    a pawl pivotably coupled to the tension actuator handle;
    a containment sleeve received in the cylindrical housing;
    a plurality of spring washers received in the containment sleeve;
    a gauge collar connected to a proximal end of the containment sleeve;
    an outer sleeve coupled to and movable relative to the housing, the outer sleeve having a proximal ratcheted surface;
    a movable jaw-retaining tubular shaft received in a distal portion of the outer sleeve;
    a plurality of movable jaws supported in a tapered portion of the jaw-retaining shaft;
    a movable tubular post passing through the gauge collar, the spring washers and the jaw-retaining shaft; and
    a jaw spring biasing the jaws in a closed position.

* * * * *

UNITED STATES PATENT AND TRADEMARK OFFICE
CERTIFICATE OF CORRECTION

| | |
|---|---|
| PATENT NO. | : 8,096,998 B2 |
| APPLICATION NO. | : 11/861446 |
| DATED | : January 17, 2012 |
| INVENTOR(S) | : Jeffery Cresina |

It is certified that error appears in the above-identified patent and that said Letters Patent is hereby corrected as shown below:

Column 1,
Line 2, insert heading --INTRODUCTION--.

Column 2,
Line 17, after "associated" insert --with--.

Column 2,
Line 21, after "in" delete "an".

Column 3,
Line 3, replace "surrounds" with --surround--.

Column 3,
Lines 44-45, replace "outer sleeve 146." with --outer sleeve 102.--.

Column 3,
Line 54, after "pair" insert --of--.

Signed and Sealed this
Thirteenth Day of March, 2012

David J. Kappos
*Director of the United States Patent and Trademark Office*